United States Patent

Cordi et al.

Patent Number: 5,670,493
Date of Patent: Sep. 23, 1997

[54] AMINOPHENYLPHOSPHONIC ACID COMPOUNDS

[75] Inventors: Alex Cordi, Suresnes; Patrice Desos, Courbevoie; Angela D. Morris, Montigny Le Bretonneux; Ghanem Atassi, Saint Cloud, all of France

[73] Assignee: Adir et Compagnie, Courbevoie, France

[21] Appl. No.: 684,469

[22] Filed: Jul. 19, 1996

[30] Foreign Application Priority Data

Jul. 21, 1995 [FR] France ................................ 95 08821

[51] Int. Cl.⁶ .............. A61K 31/66; A61K 31/665; A61K 31/67; A61K 31/675; C07F 9/38; C07F 9/40; C07F 9/572; C07F 9/655; C07F 9/6553
[52] U.S. Cl. .................. 514/80; 514/95; 514/99; 514/107; 548/414; 549/6; 549/218; 558/162; 562/14
[58] Field of Search ................ 514/80, 95, 99, 514/107; 548/414; 549/6, 218; 558/162; 562/14

Primary Examiner—Johann Richter
Assistant Examiner—Michael G. Ambrose
Attorney, Agent, or Firm—The Firm of Gordon W. Hueschen

[57] ABSTRACT

A compound of formula (I):

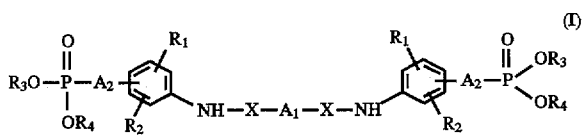

in which:

$R_1$, $R_2$, which may be identical or different, represent hydrogen or halogen, or alkyl, alkoxy, nitro or trihalomethyl, X represents CO, $SO_2$ or $CH_2$, $A_1$ represents any one of the groups as defined in the description, $A_2$ represents $-(CH_2)_n$ or $-CH=CH-$, $R_3$, $R_4$, which may be identical or different, represent hydrogen or alkyl, its isomers as well as its addition salts with a pharmaceutically acceptable base and medicinal product containing the same are useful as angiogenesis inhibitors.

14 Claims, No Drawings

AMINOPHENYLPHOSPHONIC ACID COMPOUNDS

BACKGROUND OF THE INVENTION

The present invention relates to new aminophenylphosphonic acid compounds.

1. Field of the Invention

Angiogenesis (or neovascularization) is defined as the development and growth of new capillary blood vessels. The process of angiogenesis is essential in numerous physiological situations, including embryo development, normal wound healing and the development of the endometrium after menstruation. Outside of these situations, angiogenesis in normal adults is very rare, and the mitosis of the endothelial cells which generates the walls of blood vessels is very slow, with cellular renewal times measured in years.

An abnormal angiogenesis (that is to say stimulation of the growth of new blood vessels due to a pathological syndrome) is an established characteristic for many diseases, in particular diabetic retinopathy, rheumatoid arthritis, hemangiomas and the growth of solid tumors as well as in the development of metastases.

In the oncology field, it has been shown that the growth of solid tumors is absolutely dependent on the constant development of new blood vessels, and that it is correlated, for the metastases of certain cancers, with the increasing size of the primary tumor (J. Folkman, *New Engl. Med.*, 285 (1974), 1182–1185).

A pharmaceutical treatment using an angiogenesis inhibitor may hence stop the growth of primary tumors, prevent or reduce the formation of metastases and prevent the appearance of secondary tumors. Such angiogenesis inhibitors are also useful in the treatment of non-neoplastic diseases mentioned above, in which an angiogenic activity is apparent.

The requirements of therapy demand the constant development of new angiogenesis-inhibiting compounds with the object of obtaining active principles which are both more active, more specific and less toxic.

2. Description of the Prior Art

Among angiogenesis inhibitors, suramin is a well-known example. Moreover, some suramin derivatives have been studied in the literature; this applies, in particular, to the compounds described by K. D. Jentsch et al. (*J. Gen. Virol.*, 68, 2183–2192, 1987) or in Patent WO 90/15816.

The compounds of the present invention, apart from the fact that they are new, have the advantage of being especially potent without displaying particular cytotoxicity, in contrast to suramin and its derivatives described in the prior art. Moreover, they present a real activity against reproductive cycle of HIV.

DETAILED DESCRIPTION OF THE INVENTION

The invention relates more specifically to the compounds of formula (I):

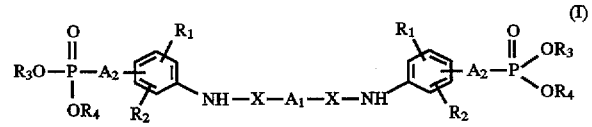

in which:

$R_1$, $R_2$, which may be identical or different, represent a hydrogen or halogen atom, a linear or branched ($C_1$–$C_6$) alkyl group, a linear or branched ($C_1$–$C_6$) alkoxy group, a nitro group or a trihalomethyl group, X represents CO, $SO_2$ or $CH_2$, $A_1$ represents a linear or branched ($C_1$–$C_{20}$) alkylene chain containing from 0 to 6 double bonds and in which one or more —$CH_2$— groups of the chain are optionally replaced by any one of the following groups:
phenylene, substituted or unsubstituted,
naphthylene, substituted or unsubstituted,
anthracenylene, substituted or unsubstituted,
($C_3$–$C_7$) cycloalkylene,

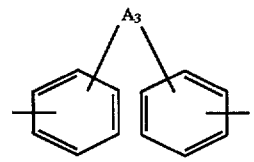

in which $A_3$ represents —$(CH_2)_m$ (in which m represents 0, 1 or 2), —(CH=CH)— ou $SO_2$,

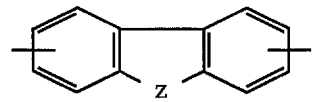

in which Z represents O, S or $NR_5$ (in which $R_5$ represents a hydrogen atom or linear or branched ($C_1$–$C_6$) alkyl group),

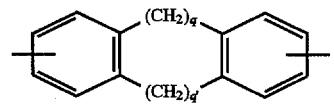

in which q and q', which may be identical or different, represent 0, 1 or 2,

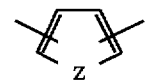

in which Z is as defined above, $A_2$ represents:
—$(CH_2)_n$— in which n is equal to 0, 1, 2 or 3,
or —CH=CH—, $R_3$, $R_4$, which may be identical or different, represent a hydrogen atom or a linear or branched ($C_1$–$C_6$) alkyl group, their isomers as well as their addition salts with a pharmaceutically acceptable acid or base.

Among pharmaceutically acceptable acids, hydrochloric, hydrobromic, sulfuric, phosphonic, acetic, trifluoroacetic, lactic, pyruvic, malonic, succinic, glutaric, fumaric, tartaric, maleic, citric, ascorbic, methanesulfonic, camphoric, and the like, acids may be mentioned without implied limitation.

Among pharmaceutically acceptable bases, sodium hydroxide, potassium hydroxide, triethylamine, tert-butylamine, and the like, may be mentioned without implied limitation.

Phenylene group, substituted or unsubstituted, naphthylene group, substituted or unsubstituted or anthracenylene group, substituted or unsubstituted, is understood to mean optionally substituted with one or more halogen atoms or linear or branched ($C_1$–$C_6$) alkyl, linear or branched ($C_1$–$C_6$) trihaloalkyl, linear or branched ($C_1$–$C_6$) alkoxy, hydroxyl, nitro, cyano, or amino (optionally substituted with one or more linear or branched ($C_1$–$C_6$) alkyl groups) groups.

The invention also extends to the process for preparing the compound of formula (I), wherein an amine of the formula (II):

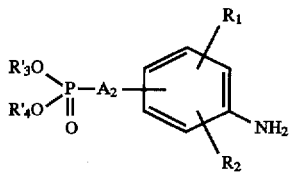
(II)

in which $R_1$, $R_2$ and $A_2$ have the same meaning as in the formula (I) and $R'_3$ and $R'_4$, which may be identical or different, represent a linear or branched ($C_1$–$C_4$) alkyl group, is used as starting material, which is reacted in a basic medium with ½ equivalent of halide of formula (III):

(III)

in which Hal represents a halogen atom and X and $A_1$ have the same meaning as in the formula (I), to yield the diester of formula (I/a), a special case of the compounds of formula (I):

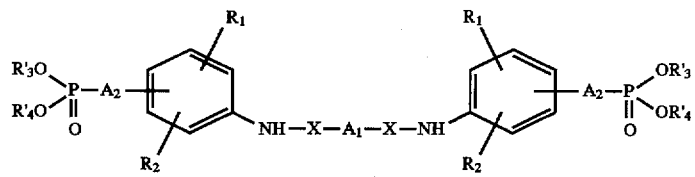
(I/a)

in which $R_1$, $R_2$, $R'_3$, $R'_4$, X, $A_1$ and $A_2$ are as defined above, which is converted to the corresponding monoester in an acid medium, a special case of the compounds of formula (I), or to the corresponding phosphonic acid in the presence of trimethylsilyl bromide, a special case of the compounds of formula (I), which diester, monoester or phosphonic acid, may be purified, where appropriate, according to a standard purification technique, is separated, where appropriate, into its isomers according to a standard separation technique, is converted, if so desired, to its addition salts with a pharmaceutically acceptable acid or base.

The compounds of formula (II) are obtained from the amine of formula (V):

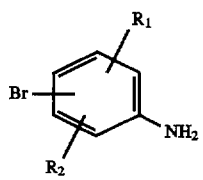
(V)

in which $R_1$ and $R_2$ have the same meaning as in the formula (I), which is protected using a protecting group such as benzyl bromide in a basic medium, to yield the compound of formula (VI):

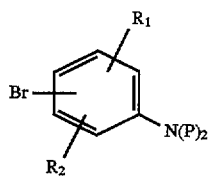
(VI)

in which $R_1$ and $R_2$ have the same meaning as in the formula (I) and P represents a protecting group, which is reacted with a dialkyl phosphite in the presence of a catalyst, to yield the compound of the formula (VII):

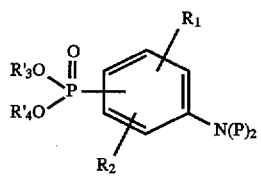
(VII)

in which $R_1$, $R_2$ and P have the same meaning as in the formula (VI) and $R'_3$ and $R'_4$, which may be identical or different, represent a linear or branched ($C_1$–$C_4$) alkyl group, the amine function of which is deprotected to yield the corresponding compound of formula (II).

The substituents $R_1$ and $R_2$ of the compound of formula (I) are obtained either by using the appropriately substituted compound of formula (II) as starting material, or by introducing the chosen substituent at the end of the synthesis according to standard techniques for substituting the aromatic ring.

The compounds of formula (I) containing a double bond in A can undergo, where appropriate, a reduction to yield the corresponding hydrogenated compounds of formula (I).

The subject of the present invention is also pharmaceutical compositions containing as active principle at least one compound of formula (I), alone or in combination with one or more nontoxic, inert excipients or vehicles.

Among the pharmaceutical compositions according to the invention, there may be mentioned, more especially, those which are suitable for oral, parenteral or nasal administration, simple or sugar-coated tablets, sublingual tablets, hard gelatin capsules, troches, suppositories, creams, ointments, skin gels, and the like.

The useful dosage varies according to the patient's age and weight, the nature and severity of the complaint and also the administration route. The latter may be oral, nasal, topical, rectal or parenteral. Generally speaking, single doses range between 1 mg and 1000 mg, for a treatment administered in 1 to 3 doses per 24 hours.

The examples which follow illustrate the invention and in no way limit it.

The preparations which follow yield synthesis intermediates which are useful in the preparation of the compounds of the invention.

The structures of the compounds of the invention were confirmed by standard spectroscopic techniques (nuclear magnetic resonance, infrared, mass spectrometry, etc.).

Preparation A

4-Aminophenylphosphonic acid diethyl ester

Stage A: 4-Bromophenyldibenzylamine

Pyridine (56.3 ml, 0.698 mol) is added to a solution of p-bromoaniline (50 g, 0.290 mol) in acetonitrile (500 ml) at 5° C., and benzylbromide (84 ml, 0.698 mol) is then added dropwise. The mixture is stirred overnight at room temperature and then 1 hour under reflux. The acetonitrile is evaporated off and the residue is taken up in dichloromethane. The organic phase is washed with 1N HCl and then saturated NaCl, dried over sodium sulfate and evaporated to give 68.5 g of a mixture of mono- and dibenzylated (50:50) product. The mixture is separated by chromatography on silica (cyclohexane/ethyl acetate, 70:30) and yields the expected product.

Melting point: 123° C.

Stage B: 4-Dibenzylaminophenylphosphonic acid diethyl ester

A solution of 50 ml of THF and 10 ml of DMF containing 27 g of the compound described in Stage A, 23 ml (178 mmol) of diethyl phosphite, 25 ml (179 mmol) of triethylamine and 3.5 g (approximately 3.5 mol %) of tetrakistriphenylphosphinePd(0) is heated to reflux and under a stream of nitrogen. After 1 hour of reflux, a further 1.6 g of tetrakistriphenylphosphinePd(0) is added and refluxing is continued for 8 h. A further 10 ml of THF, 10 ml of triethylamine and 1.5 g of tetrakistriphenylphosphinePd (0) are added. Heating under reflux is continued for 24 h. A yellow precipitate (catalyst) is filtered off from the reaction medium, the filtrate is concentrated and the residue is taken up in ethyl acetate. The organic phase is washed with 1N HCl and then saturated NaCl and dried over magnesium sulfate. The crude reaction product (38 g) is chromatographed on silica, eluting with a 50:50 cyclohexane/ethyl acetate mixture and then 100% ethyl acetate, and yields the expected product.

Stage C: 4-Aminophenylphosphonic acid diethyl ester

The compound described in Stage B above (10 g) is dissolved in 400 ml of ethanol and hydrogenated in the presence of 2 g of wet 10% Pd/C at 3 bars in a Parr apparatus while heating to 60° C. for 24 h. The catalyst is filtered off and the filtrate is evaporated to dryness to yield 7 g of pure 4-aminophenylphosphonic acid diethyl ester.

Melting point: 112°–116° C.

| | Elemental microanalysis: | | |
|---|---|---|---|
| | C % | H % | N % |
| calculated | 52.40 | 7.04 | 6.11 |
| found | 52.61 | 7.06 | 5.97 |

Preparation B

3-Aminophenylphosphonic acid diethyl ester

The expected product is obtained according to the process described in Preparation A, using 3-bromoaniline as starting material.

Preparation C

3-Aminophenyl-1,5-diphosphonic acid diethyl ester

The expected product is obtained according to the process described in Preparation A, using 3,5-dibromoaniline described in J. Org. Chem. 24, 595–598, 1959 as starting material.

Preparation of the diacid chlorides

The diacid chlorides were prepared from the corresponding dicarboxylic acids by treatment with thionylchloride. The dicarboxylic acids are either standard commercial products, or are obtained as described in the following preparations:

Preparation D

N-Ethylcarbazole-3,6-dicarboxylic acid

N-Ethylcarbazole-3,6-dicarboxylic acid was prepared according to the process described in Patent U.S. Pat. No. 4,599,399.

Preparation E

N-Ethylcarbazole-3,6-diacrylic acid

Stage A: 3,6-Diformyl-N-ethylcarbazole

LiAlH$_4$ (2.15 g, 56.3 mmol) is added portionwise to a suspension of N-ethylcarbazole-3,6-dicarboxylic acid (5.7 g, 20.12 mmol) in 160 ml of anhydrous THF cooled to 0° C. The suspension is stirred for 1 h 30 min at room temperature and then 1 hour under reflux. After cooling to 0° C., the excess hydride is hydrolyzed with a little water and the salts are filtered off. The filtrate is evaporated to dryness and dried under vacuum to give a yellow solid. The latter is suspended in dichloromethane in the presence of activated manganese dioxide (4 g, 15.16 mmol), and the mixture is stirred overnight at room temperature. 4 g of activated manganese dioxide are added and the mixture is stirred for a further 24 h. The suspension is filtered and the filtrate is evaporated under vacuum to give the expected product.

Melting point: 170°–174° C.

| | Elemental microanalysis: | | |
|---|---|---|---|
| | C % | H % | N % |
| calculated | 76.48 | 5.21 | 5.57 |
| found | 76.59 | 5.42 | 5.60 |

Stage B: N-Ethylcarbazole-3,6-diacrylic acid diethyl ester 5.25M sodium methoxide (2.47 ml, 13 mmol) is added to a suspension of the compound obtained in the preceding stage (1.55 g, 6.17 mmol) in 30 ml of methanol, and trimethyl phosphonoacetate (2.0 ml, 12.35 mmol) is then added dropwise. The suspension is stirred for 1 h at room temperature. The solvent is evaporated off under vacuum and the residue is taken up in water. The white precipitate which has formed is filtered off, rinsed with a little water and then acetonitrile and dried under vacuum to give the expected product.

Melting point: 164°–168° C.

| | Elemental microanalysis: | | |
|---|---|---|---|
| | C % | H % | N % |
| calculated | 72.71 | 5.82 | 3.85 |
| found | 72.15 | 5.65 | 3.78 |

Stage C: N-Ethylcarbazole-3,6-diacrylic acid

The diester obtained in the preceding stage is heated to 100° C. for 3 h in 30 ml of 1N NaOH. The mixture is allowed to return to room temperature and some insoluble matter is filtered off. The filtrate is acidified with 3N HCl and the precipitate is filtered off.

Melting point: 290°–300° C.

| | Elemental microanalysis: | | |
|---|---|---|---|
| | C % | H % | N % |
| calculated | 71.63 | 5.11 | 4.18 |
| found | 71.54 | 5.20 | 3.95 |

Preparation F 9,10-Dihydroanthracene-2,6-dicarboxylic acid

A solution of oxalyl chloride (6.07 ml, 69.3 mmol) in 50 ml of dichloromethane and then a solution of 9,10-dihydroanthracene in 50 ml of dichloromethane are added dropwise and with stirring to a suspension of aluminum chloride (9.24 g, 69.3 mmol) in 50 ml of dichloromethane cooled to −10° C. The suspension is stirred for 4 h at −10° C. The excess aluminum chloride is hydrolyzed by adding 1N HCl dropwise, and the organic phase is rapidly washed with water and then saturated NaCl solution and dried over MgSO₄. After evaporation to dryness, the residue is taken up in thionyl chloride (50 ml). The solution is stirred overnight under reflux. After evaporation to dryness, the residue is taken up in 100 ml of anhydrous methanol. The solution is stirred overnight under reflux and then concentrated to 50 ml. The precipitate is filtered off to give 9,10-dihydroanthracene-2,6-dicarboxylic acid dimethyl ester and the 3,6-position isomer. This mixture is saponified at 60° C. in 25 ml of 1N NaOH. After acidification by adding 1N HCl, the precipitate is filtered off to give the expected product.

Preparation G

Benzene-1,4-diacrylic acid

Stage A: Benzene-1,4-diacrylic acid dimethyl ester

Trimethyl phosphonoacetate (22 ml, 135 mmol) is added dropwise to a solution of terephthalaldehyde (9.0 g, 67.1 mmol) in 75 ml of methanol and 27 ml of 5.25M sodium methoxide (141 mmol). After gentle warming, a precipitate forms. The suspension is stirred for 1 hour at room temperature. The solvent is evaporated off under vacuum and the residue is taken up in water. The white precipitate is filtered off, rinsed with a little water and then ether and dried under vacuum to give the expected product.

Melting point: 163°–167° C.

| | Elemental microanalysis: | |
|---|---|---|
| | C % | H % |
| calculated | 68.28 | 5.73 |
| found | 68.00 | 5.65 |

Stage B: Benzene-1,4-diacrylic acid

A suspension of the above ester (7.0 g, 28.4 mmol) in 200 ml of 1N NaOH is stirred under reflux overnight. After cooling to room temperature, the reaction medium is acidified with 6N HCl and the white precipitate is filtered off to give the expected product.

Melting point: >300° C.

| | Elemental microanalysis: | |
|---|---|---|
| | C % | H % |
| calculated | 68.28 | 5.73 |
| found | 68.00 | 5.68 |

Preparation H

Benzene-1,3-diacrylic acid

The expected product is obtained according to the process described in Chem. Ber., 92, 2532–2542, 1959.

Preparation I

Diphenylmethane-4,4'-diacrylic acid

The compound is prepared according to the process described in Preparation G, using 4,4'-diformyldiphenylmethane.

Preparation J

Diphenylmethane-3,3'-dicarboxylic acid

The expected product is obtained according to the process described in Chem. Ber., 27, 2321–2326, 1894.

Preparation K

Dibenzosuberane-1,3-diacrylic acid

The compound is prepared from dibenzosuberane by a Friedel-Crafts reaction according to the process described in Preparation F, followed by a homologation reaction according to the process described in Preparation E.

Preparation L

Cyclohexane-1,4-trans-dipropionic acid

Stage A: trans-1,4-Diformylcyclohexane 41.2 g (191 mmol) of pyridinium chlorochromate are added in several portions to a suspension of trans-1,4-bis(hydroxymethyl)cyclohexane (13.8 g, 96 mmol) in 300 ml of dichloromethane. After 1 h 30 min of stirring at room temperature, a further 4 g of pyridinium chlorochromate are added and stirring is continued for 15 min. The reaction medium is filtered through Celite and the filtrate is passed through silica. After evaporation, an oil is obtained, which is used in Stage B without further purification.

Stage B: Cyclohexane-1,4-trans-dipropionic acid

By a Wittig reaction according to Stage A of Preparation G, followed by a catalytic hydrogenation and then a saponification as described in Stage B of Preparation G.

Melting point: 228°–232° C.

| | Elemental microanalysis: | |
|---|---|---|
| | C % | H % |
| calculated | 63.14 | 8.83 |
| found | 62.42 | 8.51 |

Preparation M

Furan-2,5-diacrylic acid

The compound is prepared from 2,5-furandimethanol according to the process described in Preparation E.

Melting point: 292°–296° C.

Preparation N

Thiophene-2,5-diacrylic acid

Prepared from thiophene-2,5-dicarboxylic acid according to the process described in Preparation E.

Melting point: >300° C.

| | Elemental microanalysis: | | |
|---|---|---|---|
| | C % | H % | S % |
| calculated | 53.56 | 3.60 | 14.30 |
| found | 53.54 | 3.90 | 13.91 |

Preparation O

Naphthalene-2,6-diacrylic acid

Prepared from naphthalene-2,6-dicarboxylic acid according to the process described in Preparation E.

Melting point: >260° C.

Preparation P

Fluorene-2,5-diacrylic acid

The compound is prepared from fluorene by a Friedel-Crafts reaction according to the process described in Preparation F, followed a homologation reaction according to the process described in Preparation E.

Melting point: >300° C.

| | Elemental microanalysis: | |
|---|---|---|
| | C % | H % |
| calculated | 74.50 | 4.61 |
| found | 74.80 | 4.44 |

Preparation Q

Naphthalene-1,4-diacrylic acid (17:23 cis/trans mixture)

Prepared from naphthalene-1,4-dicarboxylic acid according to the process described in Preparation E. Naphthalene-1,4-diacrylic acid is obtained in the form of a cis/trans (17:23) mixture.

Preparation R

Cyclohexane-1,4-trans-diacrylic acid

Prepared according to Preparation L, excluding the catalytic hydrogenation step.

Melting point: 299°–303° C.

| | Elemental microanalysis: | |
|---|---|---|
| | C % | H % |
| calculated | 64.27 | 7.19 |
| found | 63.88 | 6.89 |

Preparation S

4-Aminostyrylphosphonic acid diethyl ester

Stage A: 4-Nitrostyryl phosphonic acid diethyl ester

Sodium ethylate (4.95 g, 72.8 mmol) is added to a solution of 4-nitrobenzaldehyde (10 g, 66.2 mmol) in 200 ml of methanol, and tetraethyl methylenediphosphonate (21 g, 72.8 mmol) is then added dropwise. After 2 h of stirring at room temperature, a further 0.43 g of sodium ethylate and 2 g of tetraethyl methylene diphosphonate are added. After 15 min of stirring at room temperature, the ethanol is evaporated off under vacuum and the residue is bipartitioned in a water/ethyl acetate mixture. The organic phase is washed with water, then dried (MgSO$_4$) and evaporated under vacuum to give the expected product.

Melting point: 95°–98° C.

| | Elemental microanalysis: | | |
|---|---|---|---|
| | C % | H % | N % |
| calculated | 50.53 | 5.65 | 4.91 |
| found | 50.62 | 5.71 | 4.82 |

Stage B: 4-Aminostyrylphosphonic acid diethyl ester

A suspension containing 4-nitrostyrylphosphonic acid diethyl ester (3.0 g, 10.5 mmol), iron powder (5.58 g, 100 mmol) and ammonium chloride (5.58 g, 104 mmol) is heated to reflux for 45 minutes. The reaction medium is filtered through Celite. The filtrate is concentrated under vacuum and is bipartitioned in a water/dichloromethane mixture. The organic phase is washed with water, then dried (MgSO$_4$) and evaporated under vacuum to give the expected product, which crystallizes gradually.

Melting point: 81° C.

| | Elemental microanalysis: | | |
|---|---|---|---|
| | C % | H % | N % |
| calculated | 56.47 | 7.11 | 5.49 |
| found | 56.35 | 7.00 | 5.42 |

Preparation T

Benzene-1,4-di(1,3-trans-trans-butadienylene) dicarboxylic acid

Stage A: Benzene-1,4-di(1,3-trans-trans-butadienylene) dicarboxylic acid diethyl ester 8.2 ml (16.4 mmol) of 2M butyllithium in pentane are added to a solution of triethyl 4-phosphonocrotonate (4.3 ml, 19.4 mmol) in 10 ml of THF at −70° C. The mixture is stirred for 15 min at −70° C., and 1 g (7.46 mmol) of terephthalaldehyde dissolved in 15 ml of THF is added dropwise. The mixture is allowed to return to room temperature over approximately 3 hours and 75 ml of aqueous saturated NaCl solution are added (dropwise at the beginning). The reaction is extracted with ethyl acetate, and the organic phases are combined, washed with saturated NaCl solution and dried over magnesium sulfate. After evaporation under vacuum, the expected product is obtained in the form of an orange-colored solid.

Melting point: 129°–135° C.

Elemental microanalysis:

|  | C % | H % |
|---|---|---|
| calculated | 73.60 | 6.79 |
| found | 73.43 | 6.83 |

Stage B: Benzene-1,4-di(1,3-trans-trans-butadienylene) dicarboxylic acid

Melting point: >300° C.

Elemental microanalysis:

|  | C % | H % |
|---|---|---|
| calculated | 71.10 | 5.22 |
| found | 70.82 | 5.176 |

Preparation U

[2-(4-Aminophenyl)ethyl]phosphonic acid diethyl ester

Obtained after catalytic hydrogenation of 4-nitrostyrylphosphonic acid diethyl ester (Stage A of Preparation S).

Melting point: Oil

Elemental microanalysis:

|  | C % | H % | N % |
|---|---|---|---|
| calculated | 56.02 | 7.84 | 5.44 |
| found | 56.23 | 8.07 | 5.32 |

Preparation V

Anthracene-9,10-diacrylic acid

Prepared by a Wittig reaction (conditions described in Preparation G) on 9,10-anthracenedicarbaldehyde (described by K. C. MURDOCK et al., J. Med. Chem., 1982, 25, 505–519).

Melting point: >260° C.

Preparation W

2-Aminophenylphosphonic acid diethyl ester

The expected product is obtained according to the process described in Preparation A, using 2-bromoaniline as starting material.

EXAMPLE 1

4,4'-[1,8-Octanediylbis(carbonylamino)]bis (phenylphosphonic acid)tetrasodium salt

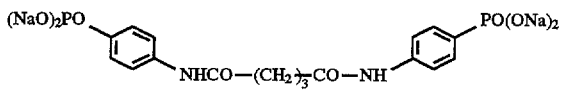

Stage A: 4,4'-[1,8-Octanediylbis(carbonylamino)]bis (phenylphosphonic acid)diethyl ester Pyridine (0.988 ml, 12.24 mmol) is added to a solution of the compound described in Preparation A (1.87 g, 8.16 mmol) in acetonitrile (15 ml), followed by a solution of sebacoyl chloride (1.12 ml, 5.23 mmol) in acetonitrile (5 ml). The mixture is stirred overnight at room temperature. The white precipitate which has formed is filtered off, rinsed with a little acetonitrile and dried under vacuum.

Melting point: 172° C.

Elemental microanalysis:

|  | C % | H % | N % |
|---|---|---|---|
| calculated | 57.69 | 7.42 | 4.48 |
| found | 57.53 | 7.24 | 4.46 |

Stage B: 4,4'-[1,8-Octanediylbis(carbonylamino)]bis (phenylphosphonic acid)

A solution of the ester obtained in Stage A (2.0 g, 3.2 mmol) in a mixture of bromotrimethylsilane (15 ml) and acetonitrile (5 ml) is stirred under reflux for 2 h. After evaporation under vacuum, the residue is stirred in methanol. A precipitate forms; it is filtered off to yield the expected acid.

Melting point: >260° C.

Elemental microanalysis:

|  | C % | H % | N % |
|---|---|---|---|
| calculated | 51.57 | 5.90 | 5.47 |
| found | 51.36 | 6.09 | 5.36 |

Stage C: 4,4'-[1,8-Octanediylbis(carbonylamino)]bis (phenylphosphonic acid)tetrasodium salt The acid obtained in Stage B (1.60 g, 3.12 mmol) is dissolved in 12.49 ml of 1N NaOH and the solution is lyophilized.

Melting point: >300° C.

Elemental microanalysis:

|  | C % | H % | N % |
|---|---|---|---|
| calculated | 44.01 | 4.37 | 4.67 |
| found | 44.07 | 4.58 | 4.62 |

The compounds described in the examples which follow are obtained according to the process described in Example 1, from the corresponding starting materials.

EXAMPLE 2

4,4'-[1,6-Hexanediylbis(carbonylamino)]bis(phenylphosphonic acid)

Starting materials:

Suberoyl chloride and compound described in Preparation A.

Stage A: 4,4'-[1,6-Hexanediylbis(carbonylamino)]bis(phenylphosphonic acid)diethyl ester Melting point: 179° C.

| Elemental microanalysis: | | | |
|---|---|---|---|
| | C % | H % | N % |
| calculated | 56.37 | 7.10 | 4.70 |
| found | 56.62 | 7.05 | 4.63 |

Stage B: 4,4'-[1,6-Hexanediylbis(carbonylamino)]bis(phenylphosphonic acid)

Melting point: >250° C.

| Elemental microanalysis: | | | |
|---|---|---|---|
| | C % | H % | N % |
| calculated | 49.80 | 5.02 | 5.81 |
| found | 49.82 | 5.44 | 5.74 |

EXAMPLE 3

4,4'-[1,7-Heptanediylbis(carbonylamino)]bis(phenylphosphonic acid)tetrasodium salt Starting materials:

Azelaoyl chloride and compound described in Preparation A.

Stage A: 4,4'-[1,7-Heptanediylbis(carbonylamino)]bis(phenylphosphonic acid)diethyl ester Melting point: 121° C.

| Elemental microanalysis: | | | |
|---|---|---|---|
| | C % | H % | N % |
| calculated | 57.04 | 7.26 | 4.59 |
| found | 56.51 | 7.20 | 4.68 |

Stage B: 4,4'-[1,7-Heptanediylbis(carbonylamino)]bis(phenylphosphonic acid)

Melting point: >250° C.

| Elemental microanalysis: | | | |
|---|---|---|---|
| | C % | H % | N % |
| calculated | 50.61 | 5.66 | 5.62 |
| found | 50.31 | 5.83 | 5.49 |

Stage C: 4,4'-[1,7-Heptanediylbis(carbonylamino)]bis(phenylphosphonic acid)tetrasodium salt Melting point: >250° C.

| Elemental microanalysis: | | | |
|---|---|---|---|
| | C % | H % | N % |
| calculated | 43.02 | 4.13 | 4.78 |
| found | 42.96 | 4.12 | 4.77 |

EXAMPLE 4

4,4'-[1,9-Nonanediylbis(carbonylamino)]bis(phenylphosphonic acid)

Starting materials:

1,11-Undecanedioic acid chloride and compound described in Preparation A.

Stage A: 4,4'-[1,9-nonanediylbis(carbonylamino)]bis(phenylphosphonic acid)diethyl ester Stage B: 4,4'-[1,9-nonanediylbis(carbonylamino)]bis(phenylphosphonic acid)

Melting point: >250° C.

| Elemental microanalysis: | | | |
|---|---|---|---|
| | C % | H % | N % |
| calculated | 52.47 | 6.13 | 5.32 |
| found | 51.96 | 6.07 | 5.16 |

EXAMPLE 5

4,4'-[1,10-Decanediylbis(carbonylamino)]bis(phenylphosphonic acid)tetrasodium salt Starting materials:

1,12-Dodecanedioic acid chloride and compound described in Preparation A.

Stage A: 4,4'-[1,10-Decanediylbis(carbonylamino)]bisphenylphosphonic acid)diethyl ester Melting point: 137° C.

Stage B: 4,4'-[1,10-Decanediylbis(carbonylamino)]bis(phenylphosphonic acid)

Melting point: >260° C.

Stage C: 4,4'[1,10-Decanediylbis(carbonylamino)]bis(phenylphosphonic acid)tetrasodium salt Melting point: >260° C.

| Elemental microanalysis: | | | |
|---|---|---|---|
| | C % | H % | N % |
| calculated | 45.87 | 4.81 | 4.46 |
| found | 45.83 | 4.85 | 4.17 |

EXAMPLE 6

4,4'-[1,11-Undecanediylbis(carbonylamino)]-bis(phenylphosphonic acid)

Starting materials:

1,13-Tridecanedioic acid chloride and compound described in Preparation A.

Stage A: 4,4'-[1,11-Undecanediylbis(carbonylamino)]bis(phenylphosphonic acid)diethyl ester
Stage B: 4,4'-1,11-Undecanediylbis(carbonylamino)]bis(phenylphosphonic acid
 Melting point: >250° C.

Elemental microanalysis:

|  | C % | H % | N % |
|---|---|---|---|
| calculated | 54.15 | 6.54 | 5.05 |
| found | 54.33 | 6.51 | 4.88 |

EXAMPLE 7

4,4'-[1,12-Dodecanediylbis(carbonylamino)]bis(phenylphosphonic acid)

Starting materials:

1,14-Tetradecanedioic acid chloride and compound described in Preparation A.
Stage A: 4,4'-[1,12-Dodecanediylbis(carbonylamino)]bis(phenylphosphonic acid)diethyl ester
 Melting point: 128° C.

Elemental microanalysis:

|  | C % | H % | N % |
|---|---|---|---|
| calculated | 59.99 | 8.00 | 4.11 |
| found | 59.74 | 8.07 | 4.16 |

Stage B: 4,4'-[1,12-Dodecanediylbis(carbonylamino)]bis(phenylphosphonic acid)
 Melting point: >250° C.

Elemental microanalysis:

|  | C % | H % | N % |
|---|---|---|---|
| calculated | 54.93 | 6.74 | 4.93 |
| found | 54.88 | 6.90 | 4.92 |

EXAMPLE 8

4,4'-[1,13-Tridecanediylbis(carbonylamino)]bis(phenylphosphonic acid)

Starting products:

1,15-Pentadecanedioic acid chloride and compound described in Preparation A.
Stage A: 4,4'-[1,13-Tridecanediylbis(carbonylamino)]-bis(phenylphosphonic acid)diethyl ester
Stage B: 4,4'-[1,13-Tridecanediylbis(carbonylamino)]-bis(phenylphosphonic acid)
 Melting point: >250° C.

Elemental microanalysis:

|  | C % | H % | N % |
|---|---|---|---|
| calculated | 55.67 | 6.92 | 4.81 |
| found | 55.45 | 6.84 | 4.52 |

EXAMPLE 9

4,4'-[1,14-Tetradecanediylbis(carbonyl-amino)]bis(phenylphosphonic acid)

Starting materials:

1,16-Hexadecanedioic acid chloride and compound described in Preparation A.
Stage A: 4,4'-[1,14-Tetradecanediylbis(carbonylamino)]bis(phenylphosphonic acid)diethyl ester
 Melting point: 130° C.

Elemental microanalysis:

|  | C % | H % | N % |
|---|---|---|---|
| calculated | 61.00 | 8.25 | 3.95 |
| found | 61.74 | 8.30 | 3.85 |

Stage B: 4,4'[1,14-Tetradecanediylbis(carbonylamino)]bis(phenylphosphonic acid)
 Melting point: >250° C.

Elemental microanalysis:

|  | C % | H % | N % |
|---|---|---|---|
| calculated | 56.37 | 7.10 | 4.70 |
| found | 56.37 | 7.06 | 4.49 |

EXAMPLE 10

4,4'-[1,3-Phenyldiylbis(acetamino)]bis(phenylphosphonic acid)tetrasodium salt

Starting products:

Benzene-1,3-diacetic acid chloride and compound described in Preparation A.
Stage A: 4,4'-[1,3-Phenyldiylbis(acetamino)]bis(phenylphosphonic acid)diethyl ester
 Melting point: 162° C.

Elemental microanalysis:

|  | C % | H % | N % |
|---|---|---|---|
| calculated | 58.44 | 6.21 | 4.54 |
| found | 58.05 | 6.18 | 4.27 |

Stage B: 4,4'-[1,3-Phenyldiylbis(acetamino)]bis(phenylphosphonic acid)
 Melting point: >250° C.

Elemental microanalysis:

|  | C % | H % | N % |
|---|---|---|---|
| calculated | 57.25 | 4.77 | 4.95 |
| found | 57.79 | 4.19 | 5.05 |

Stage C: 4,4'-[1,3-Phenyldiylbis(acetamino)]bis(phenylphosphonic acid)tetrasodium salt Melting point: >250° C.

|  | Elemental microanalysis: | | |
|---|---|---|---|
|  | C % | H % | N % |
| calculated | 44.61 | 3.06 | 4.73 |
| found | 44.38 | 3.17 | 4.02 |

EXAMPLE 11

4,4'-[4,4'-Diphenylmethanediylbis(carbonylamino)]bis(phenylphosphonic acid)tetra-sodium salt Starting materials:

Diphenylmethane-4,4'-dicarboxylic acid chloride and compound described in Preparation A.

Stage A: 4,4'-[4,4'-Diphenylmethanediylbis(carbonylamino)]bis(phenylphosphonic acid)diethyl ester Melting point: 242°–243° C.

|  | Elemental microanalysis: | | |
|---|---|---|---|
|  | C % | H % | N % |
| calculated | 61.94 | 5.94 | 4.13 |
| found | 61.55 | 6.03 | 4.09 |

Stage B: 4,4'-[4,4'-Diphenylmethanediylbis(carbonylamino)]bis(phenylphosphonic acid)

Melting point: >250° C.

|  | Elemental microanalysis: | | |
|---|---|---|---|
|  | C % | H % | N % |
| calculated | 57.25 | 4.27 | 4.95 |
| found | 57.37 | 4.33 | 4.76 |

Stage C: 4,4,'-[4,4'-Diphenylmethanediylbis(carbonylamino)]bis(phenylphosphonic acid)tetrasodium salt Melting point: >250° C.

|  | Elemental microanalysis: | | |
|---|---|---|---|
|  | C % | H % | N % |
| calculated | 49.56 | 3.08 | 4.28 |
| found | 49.96 | 3.37 | 4.24 |

EXAMPLE 12

4,4'-[4,4'-Biphenyldiylbis(sulfonylamino)]bis(phenylphosphonic acid)tetrasodium salt Starting materials:

Biphenyl-4,4'-dicarboxylic acid chloride and compound described in Preparation A.

Stage A: 4,4'-[4,4'-Biphenyldiylbis(sulfonylamino)]-bis(phenylphosphonic acid)diethylester Melting point: >260° C.

|  | Elemental microanalysis: | | | |
|---|---|---|---|---|
|  | C % | H % | N % | S % |
| calculated | 52.17 | 5.20 | 3.80 | 8.70 |
| found | 52.22 | 5.10 | 3.74 | 9.07 |

Stage B: 4,4'-[4,4'-Biphenyldiylbis(sulfonylamino)]-bis(phenylphosphonic acid)

Melting point: >260° C.

Stage C: 4,4'-[4,4'-Biphenyldiylbis(sulfonylamino)]-bis(phenylphosphonic acid)tetrasodium salt Melting point: >280° C.

|  | Elemental microanalysis: | | | |
|---|---|---|---|---|
|  | C % | H % | N % | S % |
| calculated | 40.46 | 7.55 | 3.93 | 9.00 |
| found | 38.81 | 2.80 | 3.65 | 8.15 |

EXAMPLE 13

4,4'-[4,4'-Diphenylsulfonediylbis(carbonylamino)]bis(phenylphosphonic acid)tetrasodium salt Starting materials:

Diphenylsulfone-4,4'-dicarboxylic acid chloride and compound described in Preparation A.

Stage A: 4,4'-[4,4'-Diphenylsulfonediylbis(carbonylamino)]bis(phenylphosphonic acid)diethyl ester Melting point: 210° C.

|  | Elemental microanalysis: | | | |
|---|---|---|---|---|
|  | C % | H % | N % | S % |
| calculated | 56.04 | 5.26 | 3.84 | 4.40 |
| found | 56.83 | 5.38 | 3.89 | 4.25 |

Stage B: 4,4'-[4,4'-Diphenylsulfonediylbis(carbonylamino)]bis(phenylphosphonic acid)

Melting point: >260° C.

|  | Elemental analysis: | | | |
|---|---|---|---|---|
|  | C % | H % | N % | S % |
| calculated | 50.66 | 3.60 | 4.54 | 5.20 |
| found | 51.06 | 3.78 | 4.61 | 5.15 |

Stage C: 4,4'-[4,4'-Diphenylsulfonediylbis(carbonylamino)]bis(phenylphosphonic acid)tetrasodium salt Melting point: >250° C.

| | Elemental microanalysis: | | | |
|---|---|---|---|---|
| | C % | H % | N % | S % |
| calculated | 44.33 | 2.58 | 3.98 | 4.55 |
| found | 44.28 | 2.14 | 4.02 | 4.58 |

EXAMPLE 14

4,4'-[N-Ethylcarbazole-3,6-diylbis(carbonylamino)]bis(phenylphosphonic acid)

Starting materials:

N-Ethylcarbazole-3,6-dicarboxylic acid chloride described in Preparation D and compound described in Preparation A.

Stage A: 4,4'-[N-Ethylcarbazole-3,6-diylbis(carbonylamino)]bis(phenylphosphonic acid)diethyl ester
Melting point: 221°–225° C.

| | Elemental microanalysis: | | |
|---|---|---|---|
| | C % | H % | N % |
| calculated | 61.27 | 5.86 | 5.95 |
| found | 60.52 | 5.82 | 5.95 |

Stage B: 4,4'-[N-Ethylcarbazole-3,6-diylbis(carbonylamino)]bis(phenylphosphonic acid)
Melting point: >300° C.

| | Elemental microanalysis: | | |
|---|---|---|---|
| | C % | H % | N % |
| calculated | 56.67 | 4.25 | 7.08 |
| found | 56.94 | 4.37 | 7.03 |

EXAMPLE 15

4,4'-[(9,10-Dihydroanthracene)-2,6-diylbis(carbonylamino)]bis(phenylphosphonic acid)

Starting materials:

9,10-Dihydroanthracene-2,6-dicarboxylic acid chloride described in Preparation F and compound described in Preparation A.

Stage A: 4,4'-[(9,10-Dihydroanthracene)-2,6-diylbis(carbonylamino)]bis(phenylphosphonic acid)diethyl ester
Melting point: >260° C.
Stage B: 4,4'-[(9,10-Dihydroanthracene)-2,8-diylbis(carbonylamino)]bis(phenylphosphonic acid)
Melting point: >260° C.

EXAMPLE 16

4,4'[4,4'-Biphenyldiylbis(carbonylamino)]bis(phenylphosphonic acid)

Starting materials:

4,4'-Biphenyldicarboxylic acid chloride and compound described in Preparation A.

Stage A: 4,4'-[4,4'-Biphenyldiylbis(carbonylamino)]bis(phenylphosphonic acid)diethyl ester
Melting point: >260° C.

| | Elemental microanalysis: | | |
|---|---|---|---|
| | C % | H % | N % |
| calculated | 61.44 | 5.76 | 4.21 |
| found | 61.31 | 5.86 | 4.19 |

Stage B: 4,4'-[4,4'-Biphenyldiylbis(carbonylamino)]bis(phenylphosphonic acid)
Melting point: >260° C.

| | Elemental microanalysis: | | |
|---|---|---|---|
| | C % | H % | N % |
| calculated | 56.53 | 4.01 | 5.07 |
| found | 56.39 | 3.92 | 5.05 |

EXAMPLE 17

4,4'-[3,3'-Diphenylmethanediylbis(carbonylamino)]bis(phenylphosphonic acid)

Starting materials:

Diphenylmethane-3,3'-dicarboxylic acid chloride described in Preparation J and compound described in Preparation A.

Stage A: 4,4'-[3,3'-Diphenylmethanediylbis(carbonylamino)] bis(phenylphosphonic acid)diethyl ester

| | Elemental microanalysis: | | |
|---|---|---|---|
| | C % | H % | N % |
| calculated | 61.94 | 5.94 | 4.13 |
| found | 61.72 | 5.75 | 4.00 |

Stage B: 4,4'-[3,3'-Diphenylmethanediylbis(carbonylamino)]bis(phenylphosphonic acid)
Melting point: >260° C.

| | Elemental microanalysis: | | |
|---|---|---|---|
| | C % | H % | N % |
| calculated | 5725 | 4.27 | 4.95 |
| found | 57.37 | 4.33 | 4.76 |

EXAMPLE 18

4,4'-[4,4'-trans-Stilbenediylbis(carbonylamino)]bis(phenylphosphonic acid)tetrasodium salt Starting materials:

trans-Stilbene-4,4'-dicarboxylic acid chloride and compound described in Preparation A.

Stage A: 4,4'-[4,4'-trans-Stilbenediylbis(carbonylamino)]bis(phenylphosphonic acid)diethyl ester
Melting point: >260° C.
Stage B: 4,4'-[4,4'-trans-Stilbenediylbis(carbonylamino)]bis(phenylphosphonic acid)
Melting point: >260° C.

Elemental microanalysis:

|  | C % | H % | N % |
|---|---|---|---|
| calculated | 58.14 | 4.18 | 4.84 |
| found | 57.17 | 3.94 | 4.69 |

Stage C: 4,4'-[4,4'-trans-Stilbenediylbis(carbonylamino)]bis(phenylphosphonic acid)tetrasodium salt Melting point: >260° C.

Elemental microanalysis:

|  | C % | H % | N % |
|---|---|---|---|
| calculated | 50.47 | 3.02 | 4.20 |
| found | 50.38 | 3.02 | 4.19 |

EXAMPLE 19

4,4'-[4,4'-(1,2-Diphenylethane)diylbis(carbonylamino)]bis(phenylphosphonic acid) tetrasodium salt Starting materials:

1,2-Diphenylethane-4,4'-dicarboxylic acid chloride and compound described in Preparation A.

Stage A: 4,4'-[4,4-(1,2-Diphenylethane)diylbis(carbonylamino)]bis(phenylphosphonic acid)diethyl ester Melting point: 244° C.

Elemental microanalysis:

|  | C % | H % | N % |
|---|---|---|---|
| calculated | 62.42 | 6.11 | 4.04 |
| found | 61.85 | 5.95 | 3.88 |

Stage B: 4,4'-[4,4'-(1,2-Diphenylethane)diylbis(carbonylamino)]bis(phenylphosphonic acid)

Melting point: >260° C.

Elemental microanalysis:

|  | C % | H % | N % |
|---|---|---|---|
| calculated | 57.94 | 4.51 | 4.83 |
| found | 57.44 | 4.52 | 4.75 |

Stage C: 4,4'-[4,4'-(1,2-Diphenylethane)diylbis(carbonylamino)]bis(phenylphosphonic acid)tetrasodium salt Melting point: >260° C.

Elemental microanalysis:

|  | C % | H % | N % |
|---|---|---|---|
| calculated | 50.32 | 3.32 | 4.19 |
| found | 50.13 | 3.31 | 4.17 |

EXAMPLE 20

5,5'-[1,8-Octanediylbis(carbonylamino)]bis(phenyl-1,3-diphosphonic acid)octasodium salt Starting materials:

Sebacoyl chloride and compound described in Preparation C.

Stage A: 5,5'-[1,8-Octanediylbis(carbonylamino)]bis(phenyl-1,3-diphosphonic acid)diethyl ester Stage B: 5,5'-[1,8-Octanediylbis(carbonylamino)]bis(phenyl-1,3-diphosphonic acid)

Stage C: 5,5'-[1,8-Octanediylbis(carbonylamino)]bis(phenyl-1,3-diphosphonic acid)octasodium salt Melting point: >250° C.

Elemental microanalysis:

|  | C % | H % | N % |
|---|---|---|---|
| calculated | 31.15 | 2.85 | 3.30 |
| found | 30.94 | 2.91 | 3.33 |

EXAMPLE 21

5,5'-[4,4'-Diphenylmethanediylbis(carbonylamino)]bis(phenyl-1,3-diphosphonic acid)octasodium salt Starting materials:

Diphenylmethane-4,4'-dicarboxylic acid chloride and compound described in Preparation C.

Stage A: 5,5'-[4,4'Diphenylmethanediyl-bis(carbonylamino)]bis(phenyl-1,3-diphosphonic acid)diethyl ester Melting point: >70°–72° C.

Elemental microanalysis:

|  | C % | H % | N % |
|---|---|---|---|
| calculated | 54.32 | 6.15 | 2.95 |
| found | 54.92 | 6.69 | 2.80 |

Stage B: 5,5'-[4,4'-Diphenylmethanediylbis(carbonylamino)]bis(phenyl-1,3-diphosphonic acid)

Melting point: >250° C.

Elemental microanalysis:

|  | C % | H % | N % |
|---|---|---|---|
| calculated | 44.64 | 3.61 | 3.86 |
| found | 44.04 | 3.72 | 3.65 |

Stage C: 5,5'-[4,4'-Diphenylmethanediylbis(carbonylamino)]bis(phenyl-1,3-diphosphonic acid) octasodium salt
Melting point: >250° C.

Elemental microanalysis:

|  | C % | H % | N % |
|---|---|---|---|
| calculated | 35.94 | 2.01 | 3.10 |
| found | 35.56 | 1.79 | 3.13 |

EXAMPLE 22

3,3'-[1,8-Octanediylbis(carbonylamino)]bis(phenylphosphonic acid)

Starting materials:
Sebacoyl chloride and compound described in Preparation B.
Stage A: 3,3'-[1,8-Octanediylbis(carbonylamino)]bis-(phenylphosphonic acid)diethyl ester
Melting point: 140°–150° C.

Elemental microanalysis:

|  | C % | H % | N % |
|---|---|---|---|
| calculated | 57.69 | 7.42 | 4.48 |
| found | 57.68 | 7.55 | 4.24 |

Stage B: 3,3'-[1,8-Octanediylbis(carbonylamino)]bis-(phenylphosphonic acid)
Melting point: 217°–222° C.

Elemental microanalysis:

|  | C % | H % | N % |
|---|---|---|---|
| calculated | 51.57 | 5.90 | 5.47 |
| found | 51.29 | 5.84 | 5.39 |

EXAMPLE 23

4,4'-[1,3-Divinylenebenzenediylbis-(carbonylamino)]bis(phenylphosphonic acid)

Starting materials:
Compounds described in Preparations A and H.
Stage A: 4,4'-[1,3-Divinylenebenzenediylbis(carbonylamino)]bis(phenylphosphonic acid)diethyl ester
Melting point: 197°–204° C.

Elemental microanalysis:

|  | C % | H % | N % |
|---|---|---|---|
| calculated | 60.00 | 5.98 | 4.37 |
| found | 60.12 | 5.87 | 4.22 |

Stage B: 4,4'-[1,3-Divinylenebenzenediylbis(carbonylamino)]bis(phenylphosphonic acid)
Melting point: >300° C.

Elemental microanalysis:

|  | C % | H % | N % |
|---|---|---|---|
| calculated | 54.55 | 4.20 | 5.30 |
| found | 53.70 | 4.21 | 5.07 |

EXAMPLE 24

4,4'-[1,4-Divinylenebenzenediylbis(carbonylamino)]bis(phenylphosphonic acid)

Starting materials:
Compounds described in Preparations A and G.
Stage A: 4,4'-[1,4-Divinylenebenzenediylbis(carbonylamino)]bis(phenylphosphonic acid)diethyl ester
Melting point: 300°–305° C.
Stage B: 4,4'-[1,4-Divinylenebenzenediylbis(carbonylamino)]bis(phenylphosphonic acid)
Melting point: >300° C.

Elemental microanalysis:

|  | C % | H % | N % |
|---|---|---|---|
| calculated | 54.55 | 4.20 | 5.30 |
| found | 53.29 | 4.34 | 5.08 |

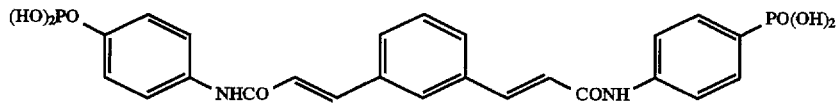

EXAMPLE 25

4,4'-[1,4-Diethylenebenzenediylbis(carbonylamino)]
bis(phenylphosphonic acid)

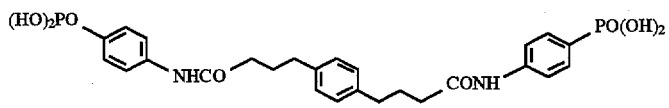

Stage A: 4,4'-[1,4-Diethylenebenzenediylbis(carbonylamino)]bis(phenylphosphonic acid)diethyl ester

The product described in Stage A of Example 24 (840 mg, 1.31 mmol) is hydrogenated in the presence of 800 mg of ammonium formate and 800 mg of palladium on charcoal in 15 ml of ethanol under reflux for 30 min. The catalyst is filtered off and the filtrate is evaporated to dryness to give the expected product.

Melting point: 264°–270° C.

Elemental microanalysis:

|  | C % | H % | N % |
|---|---|---|---|
| calculated | 59.62 | 6.67 | 4.35 |
| found | 58.89 | 6.51 | 4.32 |

Stage B: 4,4'-[1,4-Diethylenebenzenediylbis(carbonylamino)]bis(phenylphosphonic acid)

The expected product is obtained according to the process described in Stage B of Example 1.

Melting point: >260° C.

Elemental microanalysis:

|  | C % | H % | N % |
|---|---|---|---|
| calculated | 54.14 | 4.92 | 5.26 |
| found | 53.69 | 4.95 | 5.03 |

EXAMPLE 26

4,4'-[4,4'-Diethylenediphenylmethanediylbis(carbonylamino)]bis(phenylphosphonic acid)

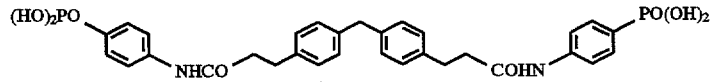

Starting materials:
Compounds described in Preparations A and I.

Stage A: 4,4'-[4,4'-(Divinylene)diphenylmethanediylbis(carbonylamino)]bis(phenylphosphonic acid)diethyl ester

Melting point: 249°–254° C.

Stage B: 4,4'-[4,4'-(Diethylene)diphenylmethanediylbis(carbonylamino)]bis(phenylphosphonic acid)diethyl ester

The product of Stage A (560 mg, 0.766 mmol) is hydrogenated in the presence of 500 mg of ammonium formate and 500 mg of palladium on charcoal in 10 ml of ethanol under reflux for 30 min. The catalyst is filtered off and the filtrate is evaporated to dryness to give the expected product.

Melting point: 80° C.

Stage C: 4,4'-[4,4'-(Diethylene)diphenylmethanediylbis(carbonylamino)]bis(phenylphosphonic acid)

Melting point: >300° C.

Elemental microanalysis:

|  | C % | H % | N % |
|---|---|---|---|
| calculated | 59.81 | 5.18 | 4.50 |
| found | 59.44 | 5.33 | 4.33 |

EXAMPLE 27

4,4'-[1,8-Octanediylbis(carbonylamino)]-bis(3-nitrophenylphosphonic acid)

Stage A: 4,4'-[1,8-Octanediylbis(carbonylamino)]bis(3-nitrophenylphosphonic acid)diethyl ester

A solution containing 1.8 ml of 96% sulfuric acid and 1.2 ml of 86% nitric acid is prepared at 0° C. 1.1 ml of this solution are withdrawn and added dropwise to a suspension at −5° C. of the compound described in Stage A of Example 1 (930 mg, 1.5 mmol) in 4.6 ml of 96% sulfuric acid. The reaction medium gradually becomes homogeneous, and after 2 h 30 min the solution is poured onto ice. The aqueous phase is extracted several times with dichloromethane and the product is purified by chromatography on silica (dichloromethane/methanol, 97:3).

Melting point: 128° C.

Elemental microanalysis:

|  | C % | H % | N % |
|---|---|---|---|
| calculated | 50.42 | 6.21 | 7.84 |
| found | 50.23 | 6.21 | 7.75 |

Stage B: 4,4'-[1,8-Octanediylbis(carbonylamino)]bis(3-nitrophenylphosphonic acid)
Melting point: 227°–230° C.

Elemental microanalysis:

|  | C % | H % | N % |
|---|---|---|---|
| calculated | 43.86 | 4.68 | 9.30 |
| found | 43.59 | 5.03 | 8.75 |

EXAMPLE 28

4,4'-[3,6-Diethylene-N-ethylcarbazolediylbis(carbonylamino)]bis(phenylphosphonic acid) tetrasodium salt Starting materials:

Compound described in Preparation A and compound obtained after catalytic reduction of the compound described in Preparation E.

Stage A: 4,4'-[3,6-Diethylene-N-ethylcarbazolediylbis(carbonylamino)]bis(phenylphosphonic acid)

Melting point: 101°–108° C.

Elemental microanalysis:

|  | C % | H % | N % |
|---|---|---|---|
| calculated | 63.07 | 6.48 | 5.52 |
| found | 62.60 | 6.45 | 5.45 |

Stage B: 4,4'-[3,6-Diethylene-N-ethylcarbazolediylbis(carbonylamino)]bis(phenylphosphonic acid)

Melting point: 279°–285° C.

Elemental microanalysis:

|  | C % | H % | N % |
|---|---|---|---|
| calculated | 59.17 | 5.12 | 6.47 |
| found | 58.96 | 5.15 | 6.28 |

Stage C: 4,4'-[3,6-Diethylene-N-ethylcarbazolediylbis(carbonylamino)]bis(phenylphosphonic acid)tetrasodium salt
Melting point: >300° C.

Elemental microanalysis:

|  | C % | H % | N % |
|---|---|---|---|
| calculated | 52.12 | 3.96 | 5.70 |
| found | 51.78 | 3.71 | 5.53 |

EXAMPLE 29

4,4'-[Dibenzosuberane-3,7-diylbis(carbonylamino)]bis(phenylphosphonic acid)tetrasodium salt
Starting materials:

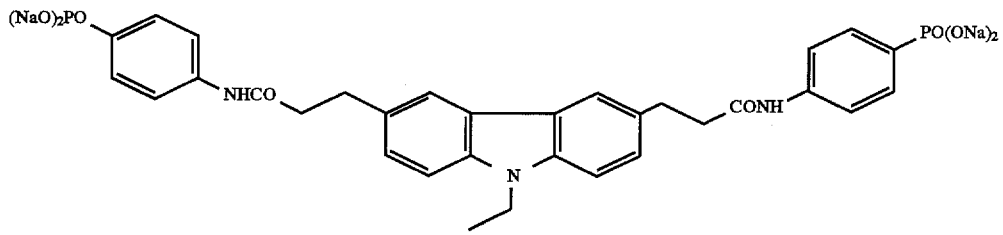

Dibenzosuberane-3,7-dicarboxylic acid chloride (prepared according to the process described in Preparation F) and compound described in Preparation A.

Stage A: 4,4'-[Dibenzosuberane-3,7-diylbis(carbonylamino)]bis(phenylphosphonic acid)diethyl ester
Melting point: 202°–205° C.

Elemental microanalysis:

|  | C % | H % | N % |
|---|---|---|---|
| calculated | 63.06 | 6.01 | 3.98 |
| found | 62.91 | 5.85 | 3.84 |

Stage B: 4,4'-[Dibenzosuberane-3,7-diylbis(carbonylamino)]bis(phenylphosphonic acid)
Melting point: 292°–296° C.

Elemental microanalysis:

|  | C % | H % | N % |
|---|---|---|---|
| calculated | 58.79 | 4.42 | 4.73 |
| found | 58.24 | 4.37 | 4.50 |

Stage C: 4,4'-[Dibenzosuberane-3,7-diylbis(carbonylamino)]bis(phenylphosphonic acid)tetrasodium salt
Melting point: >250° C.

Elemental microanalysis:

|  | C % | H % | N % |
|---|---|---|---|
| calculated | 51.19 | 3.26 | 4.12 |
| found | 51.22 | 3.77 | 4.13 |

EXAMPLE 30

4,4'-[3,6-Divinylene-N-ethylcarbazolediylbis(carbonylamino)]bis(phenylphosphonic acid) tetrasodium salt Starting materials:

Compounds described in Preparations A and E.

Stage A: 4,4'-[3,6-Divinylene-N-ethylcarbazolediylbis(carbonylamino)]bis(phenylphosphonic acid)diethyl ester Melting point: 172°–180° C.

Stage B: 4,4'-[3,6-Divinylene-N-ethylcarbazolediylbis(carbonylamino)]bis(phenylphosphonic acid)

Melting point: >300° C.

| Elemental microanalysis: | | | |
|---|---|---|---|
| | C % | H % | N % |
| calculated | 59.54 | 4.53 | 6.51 |
| found | 59.69 | 4.68 | 6.29 |

Stage C: 4,4'-[3,6-Divinylene-N-ethylcarbazolediylbis(carbonylamino)]bis(phenylphosphonic acid)tetrasodium salt Melting point: >250° C.

| Elemental microanalysis: | | | |
|---|---|---|---|
| | C % | H % | N % |
| calculated | 52.40 | 3.44 | 5.73 |
| found | 52.35 | 3.28 | 5.42 |

EXAMPLE 31

4,4'-[3,7-Divinylenedibenzosuberanediylbis(carbonylamino)]bis(phenylphosphonic acid) tetrasodium salt Starting materials:

Chloride of dibenzosuberane-1,3-diacrylic acid (Preparation K) and 4-aminophenylphosphonic acid diethyl ester (Preparation A).

Stage A: 4,4'-[3,7-Divinylenedibenzosuberanediylbis(carbonylamino)]bis(phenylphosphonic acid)diethyl ester Melting point: 179°–185° C.

| Elemental microanalysis: | | | |
|---|---|---|---|
| | C % | H % | N % |
| calculated | 65.07 | 6.13 | 3.70 |
| found | 64.53 | 6.03 | 3.58 |

Stage B: 4,4'-[3,7-Divinylenedibenzosuberanediylbis(carbonylamino)]bis(phenylphosphonic acid)

Melting point: >300° C.

| Elemental microanalysis: | | | |
|---|---|---|---|
| | C % | H % | N % |
| calculated | 61.49 | 4.69 | 4.35 |
| found | 61.44 | 4.59 | 4.12 |

Stage C: 4,4'-[3,7-Divinylenedibenzosuberanediylbis(carbonylamino)]bis(phenylphosphonic acid)tetrasodium salt Melting point: >300° C.

| Elemental microanalysis: | | | |
|---|---|---|---|
| | C % | H % | N % |
| calculated | 54.11 | 3.58 | 3.82 |
| found | 54.30 | 3.31 | 3.63 |

EXAMPLE 32

4,4'-[trans-1,4-Diethylenecyclohexanediylbis(carbonylamino)]bis(phenylphosphonic acid)

Starting materials:

trans-Cyclohexane-1,3-diacrylic acid chloride (Preparation L) and 4-aminophenylphosphonic acid diethyl ester (Preparation A).

Stage A: 4,4'-[trans-1,4-Diethylenecyclohexanediylbis(carbonylamino)]bis(phenylphosphonic acid)diethyl ester Melting point: 255°–259° C.

| Elemental microanalysis: | | | |
|---|---|---|---|
| | C % | H % | N % |
| calculated | 59.07 | 7.44 | 4.31 |
| found | 58.75 | 7.27 | 4.48 |

Stage B: 4,4'-[trans-1,4-Diethylenecyclohexanediylbis(carbonylamino)]bis(phenylphosphonic acid)

Melting point: 299°–305° C.

| Elemental microanalysis: | | | |
|---|---|---|---|
| | C % | H % | N % |
| calculated | 53.53 | 5.99 | 5.20 |
| found | 53.16 | 6.09 | 4.93 |

EXAMPLE 33

4,4'-[1,16-Hexadecanediylbis(carbonylamino)bis(phenylphosphonic acid)

Starting materials:

1,18-Octadecanedioic acid chloride and 4-aminophenylphosphonic acid diethyl ester (Preparation A).

Stage A: 4,4'-[1,16-Hexadecanediylbis(carbonylamino)]bis(phenylphosphonic acid)diethyl ester Melting point: 104° C.

Elemental microanalysis:

|  | C % | H % | N % |
|---|---|---|---|
| calculated | 61.94 | 8.48 | 3.88 |
| found | 61.99 | 8.50 | 3.53 |

Stage B: 4,4'-[1,16-Hexadecanediylbis(carbonylamino)]bis(phenylphosphonic acid)

Melting point: 245° C.

Elemental microanalysis:

|  | C % | H % | N % |
|---|---|---|---|
| calculated | 57.69 | 7.42 | 4.48 |
| found | 57.65 | 7.45 | 4.49 |

EXAMPLE 34

4,4'-[1,8-Octanediylbis(carbonylamino)]bis(benzylphosphonic acid)

Starting materials:

Sebacoyl chloride and 4-aminobenzylphosphonic acid diethyl ester.

Stage A: 4,4'-[1,8-Octanediylbis(carbonylamino)]bis(benzylphosphonic acid)diethyl ester Melting point: 178° C.

Elemental microanalysis:

|  | C % | H % | N % |
|---|---|---|---|
| calculated | 58.89 | 7.72 | 4.29 |
| found | 58.88 | 7.89 | 4.50 |

Stage B: 4,4'-[1,8-Octanediylbis(carbonylamino)]bis(benzylphosphonic acid)

Melting point: >260° C.

Elemental microanalysis:

|  | C % | H % | N % |
|---|---|---|---|
| calculated | 53.33 | 6.34 | 5.18 |
| found | 53.18 | 6.46 | 4.94 |

EXAMPLE 35

4,4'-[1,18-Octadecanediylbis(carbonylamino)]bis(phenylphosphonic acid)

Starting materials:

1,20-Eicosanedioic acid chloride and 4-aminophenylphosphonic acid diethyl ester (Preparation A).

Stage A: 4,4'-[1,18-Octadecanediylbis(carbonylamino)]bis(phenylphosphonic acid)diethyl ester Elemental microanalysis:

|  | C % | H % | N % |
|---|---|---|---|
| calculated | 62.81 | 8.70 | 3.66 |
| found | 62.65 | 8.58 | 3.54 |

Stage B: 4,4'-[1,18-Octadecanediylbis(carbonylamino)]bis(phenylphosphonic acid)

Melting point: 240° C.

Elemental microanalysis:

|  | C % | H % | N % |
|---|---|---|---|
| calculated | 58.89 | 7.72 | 4.29 |
| found | 58.78 | 7.70 | 4.10 |

EXAMPLE 36

3,3'-[1,10-Decanediylbis(carbonylamino)]bis(phenylphosphonic acid)

Starting materials:

1,12-Dodecanedioic acid chloride and 4-aminophenylphosphonic acid diethyl ester (Preparation A).

Stage A: 3,3'-[1,10-Decanediylbis(carbonylamino)]bis(phenylphosphonic acid)diethyl ester Melting point: 141°–145° C.

Elemental microanalysis:

|  | C % | H % | N % |
|---|---|---|---|
| calculated | 58.89 | 7.72 | 4.29 |
| found | 59.00 | 7.66 | 4.21 |

Stage B: 3,3'-[1,10-Decanediylbis(carbonylamino)]bis(phenylphosphonic acid)

Melting point: 195°–197° C.

Elemental microanalysis:

|  | C % | H % | N % |
|---|---|---|---|
| calculated | 53.33 | 6.34 | 5.18 |
| found | 53.02 | 6.18 | 4.99 |

EXAMPLE 37

4,4'-[1,8-Octanediylbis(carbonylamino)]bis(phenylphosphonic acid)monoethyl ester The compound of Stage A of Example 1 (600 mg, 0.96 mmol) is stirred in a mixture of 6 ml of 1N NaOH and 6 ml of ethanol at 80° C. overnight. The reaction solution is then cooled in an ice bath and acidified with 3N HCl. The white precipitate is filtered and recrystallized in ethanol.

Melting point: 191° C.

| Elemental microanalysis: | | | |
|---|---|---|---|
| | C % | H % | N % |
| calculated | 54.93 | 6.74 | 4.93 |
| found | 54.59 | 6.62 | 4.70 |

EXAMPLE 38

4,4'-[2,5-Divinylenefurandiylbis(carbonylamino)]bis(phenylphosphonic acid)

Starting materials:

Chloride of furan-2,5-diacrylic acid (Preparation M) and 4-aminophenylphosphonic acid diethyl ester (Preparation A).

Stage A: 4,4'-[2,5-Divinylenefurandiylbis(carbonylamino)]bis(phenylphosphonic acid)diethyl ester Melting point: 195°–202° C.

| Elemental microanalysis: | | | |
|---|---|---|---|
| | C % | H % | N % |
| calculated | 57.14 | 5.75 | 4.44 |
| found | 57.88 | 5.83 | 4.13 |

Stage B: 4,4'-[2,5-Divinylenefurandiylbis(carbonylamino)]bis(phenylphosphonic acid)

Melting point: >300° C.

| Elemental microanalysis: | | | |
|---|---|---|---|
| | C % | H % | N % |
| calculated | 50.98 | 3.89 | 5.40 |
| found | 50.67 | 3.91 | 5.12 |

EXAMPLE 39

4,4'-[2,5-Divinylenethiophenediylbis(carbonylamino)]bis(phenylphosphonic acid)

Starting materials:

Chloride of thiophene-2,5-diacrylic acid (Preparation N) and 4-aminophenylphosphonic acid diethyl ester (Preparation A).

Stage A: 4,4'-[2,5-Divinylenethiophenediylbis(carbonylamino)]bis(phenylphosphonic acid)diethyl ester Melting point: 249°–255° C.

| Elemental microanalysis: | | | | |
|---|---|---|---|---|
| | C % | H % | N % | S % |
| calculated | 55.72 | 5.61 | 4.33 | 4.96 |
| found | 55.43 | 5.84 | 4.46 | 4.77 |

Stage B: 4,4'-[2,5-Divinylenethiophenediylbis(carbonylamino)]bis(phenylphosphonic acid)

Melting point: >300° C.

| Elemental microanalysis: | | | | |
|---|---|---|---|---|
| | C % | H % | N % | S % |
| calculated | 49.44 | 3.77 | 5.24 | 6.00 |
| found | 49.19 | 3.75 | 5.18 | 5.75 |

EXAMPLE 40

4,4'-[2,6-Divinylenenaphthalenediylbis(carbonylamino)]bis(phenylphosphonic acid)

Starting materials:

Chloride of naphthalene-2,6-diacrylic acid (Preparation O) and 4-aminophenylphosphonic acid diethyl ester (Preparation A).

Stage A: 4,4'-[2,6-Divinylenenaphthalenediylbis(carbonylamino)]bis(phenylphosphonic acid)diethyl ester Melting point: 286°–290° C.

| Elemental microanalysis: | | | |
|---|---|---|---|
| | C % | H % | N % |
| calculated | 62.61 | 5.84 | 4.06 |
| found | 62.79 | 5.76 | 3.87 |

Stage B: 4,4'-[2,6-Divinylenenaphthalenediylbis(carbonylamino)]bis(phenylphosphonic acid)

Melting point: >260° C.

| Elemental microanalysis: | | | |
|---|---|---|---|
| | C % | H % | N % |
| calculated | 58.14 | 4.18 | 4.84 |
| found | 58.14 | 4.23 | 5.17 |

EXAMPLE 41

4,4'-[2,5-Diethylenethiophenediylbis(carbonylamino)]bis(phenylphosphonic acid)

Stage A: 4,4'-[2,5-Diethylenethiophenediylbis(carbonylamino)]bis(phenylphosphonic acid)diethyl ester The product described in Stage A Example 39 is hydrogenated as described in Example 25 in Stage A.

Melting point: 206°–212° C.

| Elemental microanalysis: | | | | |
|---|---|---|---|---|
| | C % | H % | N % | S % |
| calculated | 55.38 | 6.20 | 4.31 | 4.93 |
| found | 55.24 | 6.23 | 4.49 | 4.85 |

Stage B: 4,4'-[2,5-Diethylenethiophenediylbis(carbonylamino)]bis(phenylphosphonic acid)

Melting point: 298°–303° C.

Elemental microanalysis:

|  | C % | H % | N % | S % |
|---|---|---|---|---|
| calculated | 49.07 | 4.49 | 5.20 | 5.95 |
| found | 48.66 | 4.51 | 5.15 | 5.84 |

EXAMPLE 42

4,4'-[1,11-Undecanediylbis(carbonylamino)]bis(benzylphosphonic acid)

Starting materials:

1,13-Tridecanedioic acid chloride and 4-aminobenzylphosphonic acid diethyl ester Stage A: 4,4'-[1,11-Undecanediylbis(carbonylamino)]bis(benzylphosphonic acid)diethylester Melting point: 151°–156° C.

Elemental microanalysis:

|  | C % | H % | N % |
|---|---|---|---|
| calculated | 60.51 | 8.12 | 4.03 |
| found | 60.01 | 8.05 | 4.02 |

Stage B: 4,4'-[1,11-Undecanediylbis(carbonylamino)]bis(benzylphosphonic acid)

Melting point: 230°–236° C.

Elemental microanalysis:

|  | C % | H % | N % |
|---|---|---|---|
| calculated | 55.29 | 6.92 | 4.84 |
| found | 55.67 | 6.92 | 4.81 |

EXAMPLE 43

4,4'-[2,7-Divinylenefluorenediylbis(carbonylamino)]bis(phenylphosphonic acid)

Starting materials:

Chloride of fluorene-2,7-diacrylic acid (Preparation P) and 4-aminophenylphosphonic acid diethyl ester (Preparation A).

Stage A: 4,4'-[2,7-Divinylenefluorenediylbis(carbonylamino)]bis(phenylphosphonic acid)diethyl ester Melting point: 288°–293° C.

Elemental microanalysis:

|  | C % | H % | N % |
|---|---|---|---|
| calculated | 64.28 | 5.81 | 3.84 |
| found | 64.13 | 5.69 | 3.68 |

Stage B: 4,4'-[2,7-Divinylenefluorenediylbis(carbonylamino)]bis(phenylphosphonic acid)

Melting point: >300° C.

Elemental microanalysis:

|  | C % | H % | N % |
|---|---|---|---|
| calculated | 60.40 | 4.25 | 4.54 |
| found | 60.27 | 4.25 | 4.40 |

EXAMPLE 44

4,4'-[1,4-Divinylenenaphthalenediylbis(carbonylamino)]bis(phenylphosphonic acid)

Starting materials:

Chloride of naphthalene-1,4-diacrylic acid (Preparation Q) and 4-aminophenylphosphonic acid diethyl ester (Preparation A).

Stage A: 4,4'-[1,4-Divinylenenaphthalenediylbis(carbonylamino)]bis(phenylphosphonic acid)diethyl ester Melting point: >260° C.

Elemental microanalysis:

|  | C % | H % | N % |
|---|---|---|---|
| calculated | 62.61 | 5.84 | 4.06 |
| found | 62.24 | 5.81 | 4.03 |

Stage B: 4,4'-[1,4-Divinylenenaphthalenediylbis(carbonylamino)]bis(phenylphosphonic acid)

Melting point: >300° C.

Elemental microanalysis:

|  | C % | H % | N % |
|---|---|---|---|
| calculated | 58.14 | 4.18 | 4.84 |
| found | 58.08 | 4.21 | 4.81 |

EXAMPLE 45

4,4'-[1,4-trans-Divinylenecyclohexanediylbis(carbonylamino)]bis(phenylphosphonic acid)

Starting materials:

Chloride of cyclohexane-1,4-trans-diacrylic acid (Preparation R) and 4-aminophenylphosphonic acid diethyl ester (Preparation A).

Stage A: 4,4'-[1,4-trans-Divinylenecyclohexanediylbis(carbonylamino)]bis(phenylphosphonic acid)diethyl ester Melting point: >300° C.

Elemental microanalysis:

|  | C % | H % | N % |
|---|---|---|---|
| calculated | 59.44 | 6.86 | 4.33 |
| found | 59.31 | 6.85 | 4.34 |

Stage B: 4,4'-[1,4-trans-Divinylenecyclohexanediylbis(carbonylamino)]bis(phenylphosphonic acid)
Melting point: 300° C.

| | C % | H % | N % |
|---|---|---|---|
| calculated | 53.94 | 5.28 | 5.24 |
| found | 53.61 | 5.31 | 5.07 |

Elemental microanalysis:

EXAMPLE 46

4,4'-[1,9-Nonanediylbis(carbonylamino)]bis(styrylphosphonic acid)

Starting materials:

1,11-Undecanedioic acid chloride and 4-aminostyrylphosphonic acid diethyl ester (Preparation S).

Stage A: 4,4'-[1,9-Nonanediylbis(carbonylamino)]bis(styrylphosphonic acid)diethyl ester
Melting point: 161°–166° C.

Elemental microanalysis:

| | C % | H % | N % |
|---|---|---|---|
| calculated | 60.86 | 7.59 | 4.06 |
| found | 60.81 | 7.62 | 4.10 |

Stage B: 4,4'-[1,9-Nonanediylbis(carbonylamino)]bis(styrylphosphonic acid)
Melting point: >300° C.

Elemental microanalysis:

| | C % | H % | N % |
|---|---|---|---|
| calculated | 56.05 | 6.27 | 4.84 |
| found | 55.83 | 6.34 | 4.72 |

EXAMPLE 47

4,4'-[1,4-Di(1,3-trans-trans-butadienylene)benzenediylbis(carbonylamino)]bis(phenylphosphonic acid)

Starting materials:

Chloride of benzene-1,4-di(1,3-trans-trans-butadienylene)dicarboxylic acid (Preparation T) and 4-aminophenylphosphonic acid diethyl ester (Preparation A).

Stage A: 4,4'-[1,4-Di(1,3-trans-trans-butadienylene)benzenediylbis(carbonylamino)]bis(phenylphosphonic acid)diethyl ester
Melting point: 278°–282° C.

Elemental microanalysis:

| | C % | H % | N % |
|---|---|---|---|
| calculated | 62.42 | 6.11 | 4.04 |
| found | 62.29 | 5.96 | 3.97 |

Stage B: 4,4'-[1,4-Di(1,3-trans-trans-butadienylene)benzenediylbis(carbonylamino)]bis(phenylphosphonic acid)
Melting point: >300° C.

Elemental microanalysis:

| | C % | H % | N % |
|---|---|---|---|
| calculated | 57.94 | 4.51 | 4.83 |
| found | 57.43 | 4.35 | 4.76 |

EXAMPLE 48

4,4'-[1,13-Tridecanediylbis(carbonylamino)]bis(styrylphosphonic acid)

Starting materials:

1,15-Pentadecanedioic acid chloride and 4-aminostyrylphosphonic acid diethyl ester (Preparation S).

Stage A: 4,4'-[1,13-Tridecanediylbis(carbonylamino)]bis(styrylphosphonic acid)diethyl ester
Melting point: 111°–115° C.

Elemental microanalysis:

| | C % | H % | N % |
|---|---|---|---|
| calculated | 62.72 | 8.10 | 3.75 |
| found | 62.37 | 8.18 | 3.74 |

Stage B: 4,4'-[1,13-Tridecanediylbis(carbonylamino)]bis(styrylphosphonic acid)
Melting point: >300° C.

Elemental microanalysis:

| | C % | H % | N % |
|---|---|---|---|
| calculated | 58.67 | 6.99 | 4.41 |
| found | 58.61 | 7.06 | 4.30 |

EXAMPLE 49

4,4'-[1,9-Nonanediylbis(carbonylamino)]bis(phenylethylphosphonic acid)

Starting materials:

1,11-Undecanedioic acid chloride and [2-(4-aminophenyl)ethyl]phosphonic acid diethyl ester (Preparation U).

Stage A: 4,4'-[1,9-Nonanediylbis(carbonylamino)]bis(phenylethylphosphonic acid)diethyl ester
Melting point: 93°–95° C.

Elemental microanalysis:

| | C % | H % | N % |
|---|---|---|---|
| calculated | 60.51 | 8.12 | 4.03 |
| found | 60.28 | 8.22 | 4.06 |

Stage B: 4,4'-[1,9-Nonanediylbis(carbonylamino)]bis(phenylethylphosphonic acid)

Melting point: >300° C.

| Elemental microanalysis: | | | |
|---|---|---|---|
| | C % | H % | N % |
| calculated | 55.67 | 6.92 | 4.81 |
| found | 55.36 | 6.98 | 4.76 |

EXAMPLE 50

4,4'-[9,10-Divinyleneanthracenediylbis(carbonylamino)]bis(phenylphosphonic acid)

Starting materials:

Chloride of anthracene-9,10-diacrylic acid (Preparation V) and 4-aminophenylphosphonic acid diethyl ester (Preparation A).

Stage A: 4,4'-[9,10-Divinyleneanthracenediylbis(carbonylamino)]bis(phenylphosphonic acid)diethyl ester Melting point: >260° C.

| Elemental microanalysis: | | | |
|---|---|---|---|
| | C % | H % | N % |
| calculated | 64.86 | 5.71 | 3.78 |
| found | 64.22 | 5.65 | 3.80 |

Stage B: 4,4'-[9,10-Divinyleneanthracenediylbis(carbonylamino)]bis(phenylphosphonic acid)

Melting point: >260° C.

| Elemental microanalysis: | | | |
|---|---|---|---|
| | C % | H % | N % |
| calculated | 61.15 | 4.17 | 4.46 |
| found | 60.88 | 4.39 | 4.49 |

EXAMPLE 51

4,4'-[1,4-Divinylenebenzenediylbis(carbonylamino)]bis(benzylphosphonic acid)

Starting materials:

Benzene-1,4-diacrylic acid chloride (Preparation G) and 4-aminobenzylphosphonic acid diethyl ester.

Stage A: 4,4'-[1,4-Divinylenebenzenediylbis(carbonylamino)]bis(benzylphosphonic acid)diethyl ester Melting point: >260° C.

| Elemental microanalysis: | | | |
|---|---|---|---|
| | C % | H % | N % |
| calculated | 61.07 | 6.33 | 4.19 |
| found | 60.73 | 6.21 | 4.15 |

Stage B: 4,4'-[1,4-Divinylenebenzenediylbis(carbonylamino)]bis(benzylphosphonic acid)

Melting point: >300° C.

| Elemental microanalysis: | | | |
|---|---|---|---|
| | C % | H % | N % |
| calculated | 56.12 | 4.71 | 5.03 |
| found | 55.72 | 4.87 | 4.83 |

EXAMPLE 52

2,2'-[1,8-Octanediylbis(carbonylamino)]bis(phenylphosphonic acid)

Starting materials:

Sebacoyl chloride and 2-aminophenylphosphonic acid diethyl ester (Preparation W).

Stage A: 2,2'-[1,8-Octanediylbis(carbonylamino)]bis(phenylphosphonic acid)diethyl ester Melting point: 61°–64° C.

Stage B: 2,2'-[1,8-Octanediylbis(carbonylamino)]bis(phenylphosphonic acid)

Melting point: 102°–105° C.

| Elemental microanalysis: | | | |
|---|---|---|---|
| | C % | H % | N % |
| calculated | 51.57 | 5.90 | 5.47 |
| found | 51.86 | 6.12 | 5.48 |

EXAMPLE 53

4,4'-[1,9-Nonanediylbis(carbonylamino)]bis(phenylethylphosphonic acid)monoethyl ester Prepared by partial hydrolysis of the corresponding diethyl ester (product of stage A of Example 51).

The product of Stage A of Example 51 (1 g, 1.44 mmol) is stirred overnight at 80° C. in 20 ml of an ethanol/water (1:1) mixture. The reaction medium is then acidified at room temperature by adding 3N HCl dropwise. A white precipitate forms, which is filtered off, rinsed with a little water, dried under vacuum and recrystallized in ethanol.

Melting point: 230° C.

| Elemental microanalysis: | | | |
|---|---|---|---|
| | C % | H % | N % |
| calculated | 58.30 | 7.57 | 4.39 |
| found | 58.37 | 7.73 | 4.49 |

EXAMPLE 54

4,4'-[1,8-Octanediylbis(carbonylamino)]bis(phenylethylphosphonic acid)

Starting materials:

Sebacoyl chloride and [2-(4-aminophenyl)ethyl]phosphonic acid diethyl ester (Preparation U).

Stage A: 4,4'-[1,8-Octanediylbis(carbonylamino)]bis(phenylethylphosphonic acid)diethyl ester
Melting point: 110°–114° C.

| | Elemental microanalysis: | | |
|---|---|---|---|
| | C % | H % | N % |
| calculated | 59.99 | 7.99 | 4.12 |
| found | 60.12 | 8.19 | 4.10 |

Stage B: 4,4'-[1,8-Octanediylbis(carbonylamino)]bis(phenylethylphosphonic acid)
Melting point: >300° C.

| | Elemental microanalysis: | | |
|---|---|---|---|
| | C % | H % | N % |
| calculated | 54.93 | 6.74 | 4.93 |
| found | 54.75 | 6.78 | 4.87 |

EXAMPLE 55

4,4'-[1,10-Decanediylbis(carbonylamino)]bis(phenylethylphosphonic acid)

Starting materials:

1,12-Dodecanedioic acid chloride and [2-(4-aminophenyl)ethyl]phosphonic acid diethyl ester (Preparation U).

Stage A: 4,4'-[1,10-Decanediylbis(carbonylamino)]bis(phenylethylphosphonic acid)diethyl ester
Melting point: 133°–138° C.

| | Elemental analysis: | | |
|---|---|---|---|
| | C % | H % | N % |
| calculated | 61.00 | 8.25 | 3.95 |
| found | 61.07 | 8.47 | 3.94 |

Stage B: 4,4'-[1,10-Decanediylbis(carbonylamino)]bis(phenylethylphosphonic acid)
Melting point: >300° C.

| | Elemental microanalysis: | | |
|---|---|---|---|
| | C % | H % | N % |
| calculated | 56.37 | 7.10 | 4.70 |
| found | 56.46 | 7.27 | 4.74 |

EXAMPLE 56

4,4'-(1,10-Decanediylbisamino)bis(phenylphosphonic acid)dihydrobromide

Stage A: 4,4'-(1,10-Decanediylbisamino)bis(phenylphosphonic acid)diethyl ester

The product of Stage A of Example 1 (700 mg, 1.12 mmol) is suspended in 300 ml of THF at 0° C. A BH₃/THF solution (1M in THF, 15 ml) is added dropwise. The mixture is allowed to return to room temperature and stirring is continued overnight. The reaction solution is treated with 10 ml of methanol and is stirred for 3 days at room temperature before being concentrated. The residue is taken up in methanol and the mixture is evaporated to dryness. The product is purified by chromatography on silica (dichloromethane/methanol, 90:10).

Melting point: 158°–159° C.

| | Elemental microanalysis: | | |
|---|---|---|---|
| | C % | H % | N % |
| calculated | 60.39 | 8.45 | 4.69 |
| found | 60.33 | 8.47 | 4.64 |

Stage B: 4,4'-(1,10-Decanediylbisamino)bis(phenylphosphonic acid)dihydrobromide

The product of Stage A (320 mg, 0.536 mmol) is stirred for 1 hour under reflux in acetonitrile in the presence of 1.70 ml (6.43 mmol) of bromotrimethylsilane. The mixture is evaporated to dryness, the residue is taken up in 150 ml of methanol and the resulting mixture is stirred overnight at room temperature. It is evaporated to dryness. The residue is ground in ether and the expected product is filtered off.

Melting point: 190°–192° C.

| | Elemental microanalysis: | | | |
|---|---|---|---|---|
| | C % | H % | N % | Br % |
| calculated | 40.89 | 5.61 | 4.33 | 24.73 |
| found | 41.23 | 5.68 | 4.50 | 22.90 |

EXAMPLE 57

4,4'-[1,10-Decanediylbis(sulfonyl-amino)]bis(phenylphosphonic acid)

Starting materials:

1,10-Decanedisulfonic acid chloride and compound described in Preparation A.

Stage A: 4,4'-[1,10-Decanediylbis(sulfonylamino)]-bis(phenylphosphonic acid)diethyl ester Stage B: 4,4'-[1,10-Decanediylbis(sulfonylamino)]-bis(phenylphosphonic acid)

Pharmacological study of the compounds of the invention

EXAMPLE 58

Cytotoxicity of the compounds of the invention

Three cell lines were used:

1 murine leukemia, L1210, 1 human epidermoid carcinoma, A431, 1 primary culture of pig aorta endothelial cells, PAEC.

The cells are cultured in complete RPMI 1640 medium containing 10% of fetal calf serum, 2 mM glutamine, 50 units/ml of penicillin, 50 µg/ml of streptomycin and 10 mM HEPES (pH=7.4).

The cells are distributed in microplates and exposed to the compounds of the invention. The cells are then incubated for two days (L1210), 3 days (PAEC) and 4 days ($A_{431}$). The number of viable cells is then quantified by a colorimetric assay, the microculture tetrazolium assay (Carmichael J., DeGraff W. G., Gazdar A. F., Minna J. D. and Mitchell J. R., Evaluation of a tetrazolium-based semiautomated colorimetric assay: assessment of chemosensitivity testing, *Cancer Res.*, 47, 936–942, (1987)).

This test showed that the compounds of the invention lack cytotoxic power on the three lines studied. The $IC_{50}$ values (concentrations of test product which 50% inhibit the proliferation of the treated cells) are between 100 and 750 µM.

EXAMPLE 59

Inhibition of the neovascularization of the chick embryo chorioallantoic membrane (CAM test)

This test is carried out with chick embryos as described previously (Crum R., Szabo S. and Folkman J., Science, (1985), 230, 1375–1378). Fertilized eggs (D0) are incubated at 37° C. An air pocket is created by withdrawing 1 ml of albumin (D3), and a window is then cut in the shell (D4) and the vitelline membrane is removed to expose the chorioallantoic membrane (CAM).

The test products are solubilized in ethanol and applied to methylcellulose disks, which are dried and applied to CAM on day 6. Between 8 and 16 eggs are used per group. The zone located around the disk is then examined 48 hours later. Eggs displaying an avascular zone greater than 4 mm in diameter are counted, and the results are expressed as a percentage of eggs displaying an avascular zone. The compounds of the invention showed in this test a power to inhibit neovascularization which was greater than that of suramin. The results are collated in the following table:

| Example | Inhibition (%) of neovascularization dose (125 µM) |
| --- | --- |
| 1 | 64 |
| 5 | 68 |
| 7 | 56 |
| 8 | 90 |
| 11 | 65 |
| 24 | 82 |
| 32 | 80 |
| 39 | 75 |
| 40 | 68 |
| 44 | 80 |
| 45 | 89 |
| 47 | 93 |
| Suramin | 20 |

EXAMPLE 60

Inhibition of tumor growth in vivo in M 5076 sarcoma in mice

The malignant cells ($10^6$/mouse) are inoculated subcutaneously on day 0 to form a tumor nodule. The mice are then distributed at random in treated/control groups (12 mice/group). The compounds of the invention are administered intraperitoneally from day 1 to day 12. The inhibition of tumor growth ($I_{TG}$) is evaluated on the 13th day according to the following calculation:

$$\% I_{TG} = 100 - \left( \frac{\text{Median tumor volume of treated mice}}{\text{Median tumor volume of control mice}} \right) \times 100$$

The collective results obtained for the compounds of Examples 1 and 11 are collated below:

| | | Cytotoxicity | | |
| --- | --- | --- | --- | --- |
| Example | CAM test | PAEC $IC_{50}$ µM | L 1210 $IC_{50}$ µM | M 5076 sarcona % $I_{TG}$ |
| 1 | 64 ± 6 | >500 | >500 | 61 (60 mg/kg) |
| 11 | 65 ± 8 | 429 | >500 | 60 (30 mg/kg) |
| Suramin | 20 ± 3 | 202 ± 10 | 131 ± 21 | 67 (100 mg/kg) (d 1,4,7 i.v.) |

Thus, in contrast to suramin which shows a weak inhibition of neovascularization (CAM) and a relative cytotoxicity on the L 1210 leukemic line, the compounds of Examples 1 and 11 showed a very good correlation between antitumor activity and inhibition of angiogenesis without a cytotoxic effect.

EXAMPLE 61

Pharmaceutical composition

Preparation formula for 1000 tablets containing a 10 mg dose

| | |
| --- | --- |
| Compound of Example 2 | 10 g |
| Hydroxypropylcellulose | 2 g |
| Wheat starch | 10 g |
| Lactose | 100 g |
| Magnesium stearate | 3 g |
| Talc | 3 g |

We claim:

1. A compound selected from the group consisting of those of formula (I):

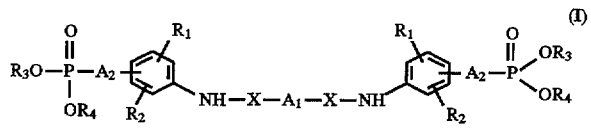

in which:

$R_1$, $R_2$, which may be identical or different, represent hydrogen, halogen, linear or branched ($C_1$–$C_6$) alkyl, linear or branched ($C_1$–$C_6$) alkoxy, nitro, or trihalomethyl, X represents CO, $SO_2$, or $CH_2$, $A_1$ represents selected from the group consisting of those linear or branched ($C_1$–$C_{20}$) alkylene chain containing 0 to 6 double bonds and in which one or more —$CH_2$— groups of the chain are optionally replaced by any one of the following groups:
phenylene, substituted or unsubstituted,
naphthylene, substituted or unsubstituted,
anthracenylene, substituted or unsubstituted,
($C_3$–$C_7$) cycloalkylene,

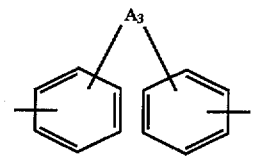

in which $A_3$ represents —($CH_2$)$_m$ in which m represents 0, 1 or 2, —(CH=CH)—, or $SO_2$,

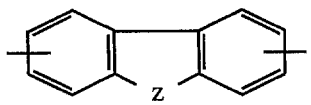

in which Z represents O, S, or $NR_5$ in which $R_5$ represents hydrogen or linear or branched ($C_1$–$C_6$)alkyl,

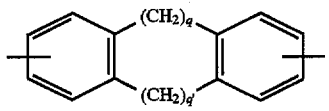

in which q or q', which may be identical or different, represent 0, 1 or 2,

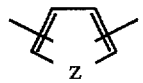

in which Z is as defined above, $A_2$ represents:
—$(CH_2)_n$— in which n is 0, 1, 2, or 3,
or —CH=CH—, $R_3$, $R_4$, which may be identical or different, represent hydrogen or linear or branched ($C_1$–$C_6$) alkyl, its isomers and its addition salts with a pharmaceutically-acceptable acid or base, the term "substituted" meaning that the relevant group is substituted with one or more halogen atoms or linear or branched ($C_1$–$C_6$) alkoxy, hydroxyl, nitro, cyano, or amino (optionally substituted with one or more linear or branched ($C_1$–$C_6$) alkyl groups) groups.

2. A compound of claim 1 wherein X represents CO.
3. A compound of claim 1 wherein X represents $SO_2$.
4. A compound of claim 1 wherein X represents $CH_2$.
5. A compound claim 1, wherein $A_1$ represents linear or branched ($C_1$–$C_{20}$) alkylene.
6. A compound of claim 1 in which $A_1$ represents a linear or branched ($C_1$–$C_{20}$) alkylene chain containing 0 to 6 double bonds and in which one or more —$CH_2$— groups of the chain are replaced by a phenylene, naphthylene, or ($C_3$–$C_7$) cycloalkylene, or

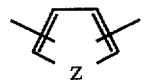

in which Z is as defined in claim 1.

7. A compound of claim 1 in which $A_1$ represents a ($C_1$–$C_{20}$) alkylene chain in which a —$CH_2$— group of the chain is replaced by

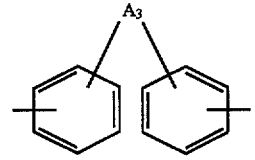

in which $A_3$ is as defined in claim 1.

8. A compound of claim 1 in which $A_2$ represents —$(CH_2)_n$— in which n is equal to 0, 1, 2, or 3.
9. A compound of claim 1 in which $A_2$ represents —CH=CH—.
10. A compound of claim 1 which is selected from the group consisting of 4,4'-[1,8-octanediylbis (carbonylamino)]bis-(phenylphosphonic acid), and an addition salts thereof with a pharmaceutically-acceptable base.
11. A compound of claim 1 which is selected from the group consisting of 4,4'-[4,4'-diphenylmethanediylbis (carbonyl-amino)]bis(phenylphosphonic acid), and an addition salts thereof with a pharmaceutically-acceptable base.
12. A compound of claim 1 which is 4,4'-[1,4-divinylenebenzenediylbis-(carbonylamino)]bis (phenylphosphonic acid).
13. A pharmaceutical composition useful as an angiogenesis inhibitor comprising as active principle an effective amount of a compound of claim 1, together with one or more pharmaceutically-acceptable excipients or vehicles.
14. A method for treating a living body afflicted with a condition requiring an angiogenesis inhibitor comprising the step of administering to the living body an amount of a compound of claim 1 which is effective for alleviation of said condition.

* * * * *

UNITED STATES PATENT AND TRADEMARK OFFICE
CERTIFICATE OF CORRECTION

PATENT NO. : 5,670,493
DATED : Sept. 23, 1997
INVENTOR(S) : Alex Cordi, Patrice Desos, Angela D. Morris, Ghanem Atassi It is certified that error appears in the above-indentified patent and that said Letters Patent is hereby corrected as shown below:

Column 9, line 51: "Preparation O" should read -- Preparation Q --.

Column 18, line 25: "7.55" should read -- 2.55 --.

Column 42, line 61: "($A_{431}$)" should read -- A431 --.

Column 44, line 48: Delete "selected from the group consisting of those".

Column 44, line 49: Insert "a" at the beginning of the line.
<u>Claim 1, line 7</u>.

Column 44, line 66: Insert a -- , -- (comma) after "1" at the end of the line.
<u>Claim 1, line 15</u>.

Column 45, line 16: Insert a -- , -- (comma) after "1".
<u>Claim 1, line 20</u>.

Column 45, line 38: Insert -- of -- between "compound" and "claim".

UNITED STATES PATENT AND TRADEMARK OFFICE
CERTIFICATE OF CORRECTION

PATENT NO.   : 5,670,493
DATED        : Sept. 23, 1997
INVENTOR(S)  : Alex Cordi, Patrice Desos, Angela D. Morris, Ghanem Atassi It is certified that error appears in the above-indentified patent and that said Letters Patent is hereby corrected as shown below:

Column 46, line 20:   Delete "equal to".
                                          Claim 8, line 2.

Column 46, line 27:   "salts" should read -- salt --.
                                          Claim 10, line 2.

Column 46, line 31:   "salts" should read -- salt --.
                                          Claim 11, line 3.

Signed and Sealed this

Ninth Day of December, 1997

Attest:

BRUCE LEHMAN

Attesting Officer                    Commissioner of Patents and Trademarks